US008822539B2

(12) United States Patent
Jensen

(10) Patent No.: US 8,822,539 B2
(45) Date of Patent: Sep. 2, 2014

(54) COMBINATION THERAPIES: INHIBITORS OF GABA TRANSAMINASE AND NKCC1

(75) Inventor: Frances E. Jensen, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 149 days.

(21) Appl. No.: 13/069,311

(22) Filed: Mar. 22, 2011

(65) Prior Publication Data

US 2011/0237554 A1 Sep. 29, 2011

Related U.S. Application Data

(60) Provisional application No. 61/318,352, filed on Mar. 28, 2010.

(51) Int. Cl.
| | | |
|---|---|---|
| *A01N 41/06* | (2006.01) | |
| *A61K 31/08* | (2006.01) | |
| *A01N 37/00* | (2006.01) | |
| *A61K 31/19* | (2006.01) | |
| *C07C 303/00* | (2006.01) | |
| *C07C 307/00* | (2006.01) | |
| *C07C 309/00* | (2006.01) | |
| *C07C 311/00* | (2006.01) | |
| *C07C 61/00* | (2006.01) | |
| *C07C 61/08* | (2006.01) | |

(52) U.S. Cl.
USPC ...................................... 514/603

(58) Field of Classification Search
USPC ..................... 514/603, 557; 564/86; 562/400
See application file for complete search history.

(56) References Cited

U.S. PATENT DOCUMENTS

| | | |
|---|---|---|
| 6,495,601 B1 | 12/2002 | Hochman |
| 7,214,711 B2 | 5/2007 | Hochman |
| 2005/0187205 A1 | 8/2005 | Lamberty et al. |
| 2006/0025387 A1 | 2/2006 | Hochman |
| 2008/0206324 A1 | 8/2008 | Gryczke et al. |
| 2009/0258844 A1 | 10/2009 | Hochman |

OTHER PUBLICATIONS

International Search Report and Written Opinion of PCT/US2011/029467, Dec. 22, 2011.
Aicardi et al., "Vigabatrin as initial therapy for infantile spasms: a European retrospective survey. Sabril IS Investigator and Peer Review Groups," Epilepsia, 37:638-642, 1996 (Abstract only).
Andre et al., "Vigabatrin protects against hippocampal damage but is not antiepileptogenic in the lithium-pilocarpine model of temporal lobe epilepsy," Epilepsy Res., 47:99-117, 2001 (Abstract only).
Bauer, "Photic release of radioactivity from rabbit retina preloaded with [3H] GABA," Acta Ophthalmol., 56:270-281, 1978 (Abstract only).
Bialer et al., "Progress report on new antiepileptic drugs: a summary of the Seventh Eilat Conference (EILAT VII)," Epilepsy Res., 61:1-48, 2004 (Abstract only).
Clift and Silverman, "Synthesis and Evaluation of Novel Aromatic Substrates and Competitive Inhibitors of GABA Aminotransferase," Bioorg. Med. Chem. Left., 18:3122-3125, 2008.
Crewther et al., "Potassium Channel and NKCC Cotransporter Involvement in Ocular Refractive Control Mechanisms," PlosOne, 3:e2839, 2008.
Cubells et al., "In vivo action of enzyme-activated irreversible inhibitors of glutamic acid decarboxylase and gamma-aminobutyric acid transaminase in retina vs. brain," J. Pharmacol. Exp. Ther. 238:508-514, 1986 (Abstract only).
Duboc et al., "Vigabatrin, the GABA-transaminase inhibitor, damages cone photoreceptors in rats," Ann. Neurol., 55:695-705, 2004 (Abstract only).
Dzhala et al., "Bumetanide enhances phenobarbital efficacy in a neonatal seizure model," Ann. Neurol., 63:222-235, 2008 (Abstract only).
Dzhala et al., "NKCC1 transporter facilitates seizures in the developing brain," Nature Med., 11:1205-1213, 2005 (Abstract only).
Follett et al., "Glutamate Receptor-Mediated Oligodendrocyte Toxicity in Periventricular Leukomalacia: A Protective Role for Topiramate," J. Neurosci., 24:4412-4420, 2004.
Follett et al., "NBQX Attenuates Excitotoxic Injury in Developing White Matter," J. Neurosci., 20:9235-9241, 2000.
International Preliminary Report on Patentability for PCT/US2011/029467, issued Oct. 2, 2012.
Jammoul et al., "Taurine deficiency is a cause of vigabatrin-induced retinal Phototoxicity," Ann. Neurol., 65:98-107, 2009.
John et al., "Micro-vacuolation in rat brains after long term administration of GABAtransaminase inhibitors. Comparison of effects of ethanolamine-Osulphate and vigabatrin," Biochem. Pharmacol., 36:1467-1473, 1987 (Abstract only).
Kahle et al., "The bumetanide-sensitive Na-K-2Cl cotransporter NKCC1 as a potential target of a novel mechanism-based treatment strategy for neonatal seizures," Neurosurg. Focus, 25:E22, 2008 (Abstract only).
Li et al., "Spatial and temporal distribution patterns of Na-K-2Cl cotransporter in adult and developing mouse retinas," Vis. Neurosci., 25:109-123, 2008 (Abstract only).
Lopez-Samblas et al., "The pharmacokinetics of bumetanide in the newborn infant," Biol. Neonate, 72:265-272, 1997 (Abstract only).
Manning et al., "NMDA Receptor Blockade with Memantine Attenuates White Matter Injury in a Rat Model of Periventricular Leukomalacia," J. Neurosci., 28:6670-6678, 2008.
Neal et al., "Immunocytochemical evidence that vigabatrin in rats causes GABA accumulation in glial cells of the retina," Neurosci. Left., 98:29-32, 1989 (Abstract only).
Pan et al., "Conformationally-restricted vigabatrin analogs as irreversible and reversible inhibitors of gamma-aminobutyric acid aminotransferase," Bioorg. Med. Chem., 12:5719-5725, 2004 (Abstract only).
Prescribing information for BUMEX (NDA 18225/S-024) dated Sep. 9, 2009.

(Continued)

*Primary Examiner* — Kendra D Carter
(74) *Attorney, Agent, or Firm* — Fish & Richardson P.C.

(57) ABSTRACT

Inhibitors of NKCC1, such as bumetanide, when coadministered with inhibitors of GABA transaminase, such as vigabatrin, attenuate both the retinal toxicity and the intramyelinic edema.

11 Claims, No Drawings

(56) References Cited

OTHER PUBLICATIONS

Project No. 1RC1NS068938-01 from NIH Research Portfolio Online Reporting Tools website (http://projectreporter.nih.gov/project_info_details.cfm?aid=7829070&icde=0), award notice date Sep. 25, 2009, project start date Sep. 30, 2009.

Putney et al., "Na-K-Cl Cotransport in Normal and Glaucomatous Human Trabecular Meshwork Cells," Invest. Ophthalmol. Vis. Sci., 40:425-434, 1999.

SABRIL (vigabatrin) prescribing information, revised Apr. 2010.

Sills, "Pre-clinical studies with the GABAergic compounds vigabatrin and tiagabine," Epileptic Disord., 5:51-56, 2003 (Abstract only).

Talos et al., "Developmental regulation of alpha-amino-3-hydroxy-5-methyl-4-isoxazole-propionic acid receptor subunit expression in forebrain and relationship to regional susceptibility to hypoxic/ischemic injury. I. Rodent cerebral white matter and cortex," J. Comp. Neurol. 497:42-60, 2006 (Abstract only).

Talos et al., "Developmental regulation of AMPA receptor subunit expression in forebrain and relationship to regional susceptibility to hypoxic/ischemic injury: Part II. Human cerebral white matter and cortex," J. Comp. Neurol., 497:61-77, 2006.

Thoreson et al., "Reciprocal Interactions Between Calcium and Chloride in Rod Photoreceptors," J. Neurophysiol., 90:1747-1753, 2003.

Wang et al., "Treatment of epilepsy: the GABA-transaminase inhibitor, vigabatrin, induces neuronal plasticity in the mouse retina," Eur. J. Neurosci., 27:2177-2187, 2008.

256
COMBINATION THERAPIES: INHIBITORS OF GABA TRANSAMINASE AND NKCC1

This application claims priority to U.S. 61/318,352 filed Mar. 28, 2010.

This work was supported by NIH Grant RC1 NS068938-01. The U.S. government has rights in any patent issuing on this application.

BACKGROUND OF THE INVENTION

The field of the invention is combination therapies of inhibitors of γ-amino butyric acid (GABA) transaminase and Na—K—Cl cotransporter (NKCC1).

Na—K—Cl cotransporter antagonists have been proposed to treat seizures (e.g. Hochman: US2009/0258844; U.S. Pat. Nos. 7,214,711; and 6,495,601), and in particular, Bumetanide has been proposed to be useful to treat neonatal seizures (Dzhala et al. Nat. Med. 2005 November; 11(11): 1205-13), and has been reported to enhance Phenobarbital efficacy in neonatal seizure model (Dzhala et al. Ann Neurol 2008, 632: 222-235)

Vigabatrin (VGB) is a known anticonvulsant that acts as an irreversible inhibitor of gamma-aminobutyric acid (GABA) transaminase, the enzyme responsible for the catabolism of the inhibitory neurotransmitter GABA. The resultant increase in brain GABA levels is thought to be the mechanism of its anticonvulsant actions in infantile spasms and for refractory seizures.

Vigabatrin is associated with well documented retinal toxicity resulting in peripheral visual field deficits and also animal models that suggest intramyelinic edema in white matter areas, and in 1998 the FDA issued a "not approvable action" on vigabatrin because of its high incidence (30%) of permanent vision loss. Hence, since at least 1998 vigabatrin has been known to be effectively contraindicated for all pharmaceutical use in the United States, including use as an anticonvulsant. On Aug. 21, 2009 the FDA provided limited approval of vigabatrin for treatment seizure and infantile spasms, but required a black box warning for permanent vision loss.

We disclose that inhibitors of NKCC1 (such as bumetanide), when coadministered with inhibitors of GABA transaminase (such as vigabatrin) attenuate the retinal toxicity and/or the intramyelinic edema, and thereby expand the indications for vigabatrin and provide the first motivation for one skilled in the art to combine these two drugs for pharmaceutical delivery.

Aspects of this disclosure were published by the inventor in NIH Grant No. RC1 NS068938-01, who also has an ongoing clinical trial entitled "Pilot Study of Bumetanide for Newborn Seizures" (NCT00830531).

SUMMARY OF THE INVENTION

The invention provides methods and compositions for treating infantile spasms or refractory adult seizures. In one aspect the invention provides pharmaceutical compositions comprising a γ-amino butyric acid (GABA) transaminase inhibitor associated with vision loss such as peripheral visual field deficits, and a Na—K—Cl cotransporter (NKCC1) inhibitor.

In particular embodiments:
the GABA transaminase inhibitor is a GABA analog selected from ethanolamine-O-sulfate, gamma-acetylenic-GABA, gamma-vinyl-GABA (vigabatrin), aminooxyacetic acid, valproate, and structural analogs thereof.

the GABA transaminase inhibitor is an optionally conformationally-constrained vigabatrin analog;

the GABA transaminase inhibitor is gamma-vinyl-GABA (vigabatrin);

the GABA transaminase inhibitor is 4-hydroxybenzaldehyde or a 4-hydroxybenzaldehyde analogue;

the GABA transaminase inhibitor is a 4-hydroxybenzaldehyde analogue selected from 3-chloro-1-(4-hydroxyphenyl)propan-1-one, and 4-acryloylphenol;

the NKCC1 inhibitor is selected from: Bumetanide, Furosemide, Ethacrynic acid and Torsemide;

the GABA transaminase inhibitor is vigabatrin, and the NKCC1 inhibitor is selected from: Bumetanide, Furosemide, Ethacrynic acid and Torsemide; and/or the GABA transaminase inhibitor is vigabatrin, and the NKCC1 inhibitor is Bumetanide.

In another aspect the invention provides an effective unit dosage of a subject composition further comprising a pharmaceutically-acceptable excipient.

In another aspect the invention provides a subject composition wherein the transaminase inhibitor and the NKCC1 inhibitor are contained in a unit dosage form.

In another aspect the invention provides a subject composition wherein the transaminase inhibitor and the NKCC1 inhibitor are copackaged.

In another aspect the invention provides a subject composition wherein the transaminase inhibitor and the NKCC1 inhibitor are coformulated.

In another aspect the invention provides a subject composition wherein the transaminase inhibitor and the NKCC1 inhibitor are coformulated and in a unit dosage form.

In another aspect the invention provides a method of treating a person in need thereof comprising administering an effective amount of a subject composition.

In particular embodiments the person is determined to have had infantile spasms or refractory seizures as an adult.

In another aspect the invention provides a method of treating a person in need thereof comprising coadministering to the person effective amounts of a γ-amino butyric acid (GABA) transaminase inhibitor and a Na—K—Cl cotransporter (NKCC1) inhibitor.

In particular embodiments the person is determined to have had infantile spasms or refractory seizures as an adult.

In another aspect the invention provides a method of treating a person treated or being treated with a γ-amino butyric acid (GABA) transaminase inhibitor, comprising administering to the person an effective amount of an NKCC1 inhibitor.

In particular embodiments:
the GABA transaminase inhibitor is gamma-vinyl-GABA (vigabatrin), and the NKCC1 inhibitor is selected from: Bumetanide, Furosemide, Ethacrynic acid and Torsemide;

the GABA transaminase inhibitor is gamma-vinyl-GABA (vigabatrin), and the NKCC1 inhibitor is Bumetanide; and/or the person is determined to have had infantile spasms or refractory seizures as an adult.

In addition the invention provides all recombinations of alternative recited elements as if each recombination were separately set forth.

DETAILED DESCRIPTION OF SPECIFIC EMBODIMENTS OF THE INVENTION

The invention provides methods and compositions for treating infantile spasms or refractory adult seizures.

In one aspect the invention provides pharmaceutical compositions comprising a γ-amino butyric acid (GABA) transaminase inhibitor and a Na—K—Cl cotransporter (NKCC1) inhibitor.

The GABA transaminase inhibitor component is typically a competitive inhibitor of the GABA transaminase, and typically also a structural analog or isomer of GABA, though it may be further conformationally-constrained, such as with stearically-hindered moieties, or additional bonding, particularly ring bonding. In particular embodiments the GABA transaminase inhibitor is a GABA analog such as ethanolamine-O-sulfate, gamma-vinyl-GABA (vigabatrin), gamma-acetylenic GABA, aminooxyacetic acid, valproate, or a structural analog or isomer thereof.

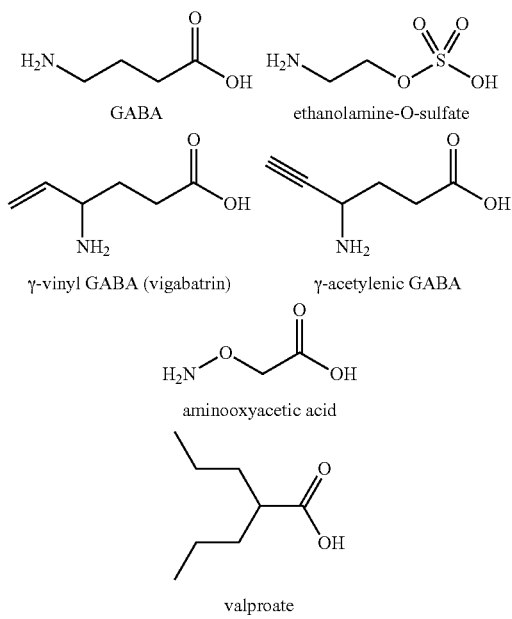

Active analogs known in the art and/or readily prepared using conventional pharmaceutical substitutions and derivitazations, such as fluor-substitution:

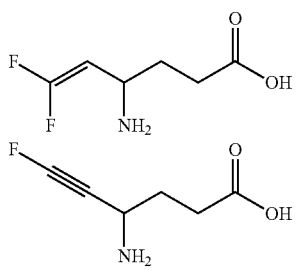

In particular embodiments the GABA transaminase inhibitor is a conformationally-constrained vigabatrin analogue having a structure, e.g.:

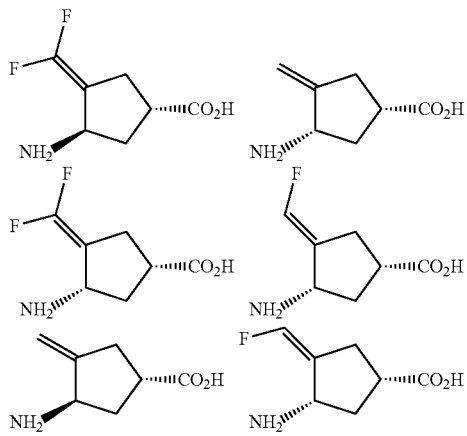

In other particular embodiments, the GABA transaminase inhibitor is 4-hydroxybenzaldehyde or a 4-hydroxybenzaldehyde analog such as 3-chloro-1-(4-hydroxyphenyl)propan-1-one, or 4-acryloylphenol:

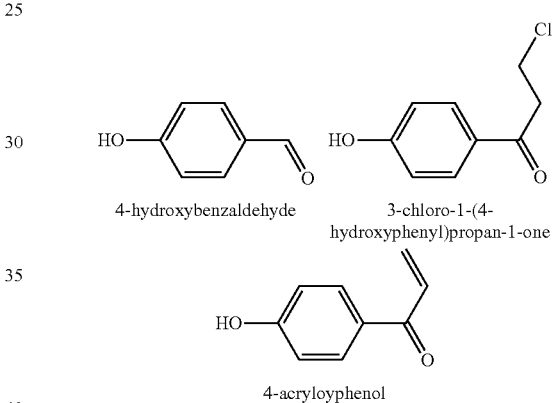

Alternative competitive inhibitors of GABA aminotransferase are known in the art, or are derivable from established transferase assays, e.g. Clift M D, Silverman R B. Bioorg Med Chem. Lett. 2008 May 15; 18(10):3122-5. For example, conformationally rigid vigabatrin analogs have been described, inter alia, by Pan et al., Bioorganic & Medicinal Chem, 12 (21) 1 Nov. 2004, 5719-5725.

The NKCC1 inhibitor component is typically a competitive inhibitor of the Na—K—Cl cotransporter, commonly known as NKCC1 inhibiting loop diuretics. Well-known examples include Bumetanide, Furosemide, Ethacrynic acid and Torsemide; however, the invention may be practiced with analogs of these drugs, or alternative pharmaceutically-acceptable NKCC1 inhibitors.

The subject compositions may be provided in effective unit dosages, typically further comprising a pharmaceutically-acceptable excipient. In particular embodiments, both the transaminase inhibitor and the NKCC1 inhibitor components are contained in the unit dosage form. The term "unit dosage forms" refers to physically discrete units suitable as unitary dosages for human subjects, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the compound may be a major or minor component with the remainder being various vehicles or carriers and processing aids helpful for forming the desired dosing form.

Suitable excipients or carriers and methods for preparing administrable compositions are known or apparent to those skilled in the art and are described in more detail in such publications as Remington's Pharmaceutical Science, Mack Publishing Co, NJ (1991). In addition, the compounds may be advantageously used in conjunction with other therapeutic agents as described herein or otherwise known in the art. Hence the compositions may be administered separately, jointly, or combined in a single dosage unit.

Dosages depend on the compounds formulation, route of administration, etc. and are established for many of the constituent GABA transaminase and NKCC1 inhibitors, or are otherwise generally empirically determined in routine trials, and variations will necessarily occur depending on the target, the host, and the route of administration, etc.

In particular embodiments fixed-dose tablets or capsules comprising 10-1000 mg vigabatrin, such as 10-100, 100-1000, 200-800, 200, 300, 400, 500, 600, or 700 mg, and 0.01-10 mg bumetanide, such as 0.01-0.1, 0.1-1, 0.1-0.5, 0.25-3, 0.1, 0.2, 0.3, 0.4 and 0.5 mg, formulated using standard excipients. Such dosages may also be administered in solution, such as IV, 1M or oral, particularly with pediatric patients.

By reducing side-effects otherwise associated with use of GABA transaminase inhibitors, particularly vigabatrin, the subject combination therapies actually permit use of increased dosages and treatment durations, beyond that safe or considered in the art to be safe or recommended if not coadministered. The combination therapies can also surprisingly, synergistically increase the potency of the component inhibitors, particularly vigabatrin and/or the NKCC1 inhibitor, particularly bumetanide, and thereby also permit use reduced dosages, and even dosages subtherapeutic, or considered in the art to be subtherapeutic, if not coadministered, while maintaining efficacy.

Hence, in particular embodiments, one or both of the inhibitor components are administered and/or packaged at an atypical dosage—a dosage significantly outside of the previously recommended dosages of the component drugs, wherein the GABA transaminase inhibitor, particularly vigabatrin, may be in excess (e.g. at least 150%, 200%, 300%, 400%, 600%, or 1000%) of its recommended (or the above recited) dosages (e.g. unit or daily dosage) or more typically, less than (e.g. at or less than 60%, 50%, 40%, 30%, 20%, 10%, 5% or 1% of) its recommended (or the above recited) dosages, and/or the NKCC1 inhibitor, particularly bumetanide, is typically less than (e.g. at or less than 60%, 50%, 40%, 30%, 20%, 10%, 5% or 1% of) its recommended (or the above recited) dosages, including dosages subtherapeutic as a diuretic if otherwise administered alone. See, e.g. US FDA-approved prescribing information for SABRIL (vigabatrin) issued February 2010; NDA 18225/S-024 for BUMEX (bumetanide) dated September 2009.

In particular embodiments the invention provides adjuvants to GABA transaminase inhibitor therapy, wherein the adjuvant comprises an amount of an NKCC1 inhibitor sufficient to reduce, prevent or attenuate one or more otherwise adverse side effects (such as retinal toxicity and intramyelinic edema) of the transaminase inhibitor, which amount may be significantly less than the recommended amount of the NKCC1 inhibitor as a diuretic, and may be subtherapeutic, if used alone, for that purpose.

As examples, effective unit dosage combination therapies of vigabatrin with an atypical adjuvant dosage of an NKCC1 inhibitor include a 500 mg vigabatrin dose combined with a bumetanide adjuvant at 0.2, 0.1, 0.05, 0.02, 0.01 mg, or a furosemide adjuvant at 8, 4, 2, 0.8, or 0.4 mg. The foregoing dosages are bases on adult, and pediatric dosages are typically adjusted (reduced) there from, according to body weight. Prior to this report no effective use of bumetanide in pediatric patients had been established, particularly infants more than 1, 2, 3 or 4 weeks old, and preferably under 36, 24 or 18 months.

The subject compositions may present the transaminase inhibitor and the NKCC1 inhibitor copackaged together, such as in a kit. For example, unit dosage forms may be copackaged in a multipack adapted for sequential use, such as blisterpack, comprising sheets of at least 6, 9 or 12 unit dosage forms. The transaminase inhibitor and the NKCC1 inhibitor components may also be coformulated, particularly in unit dosage form.

The invention also encompasses methods of treating a person in need thereof comprising administering an effective amount of a subject composition. In particular embodiments the person is determined to have had infantile spasms or refractory seizures as an adult. Infantile spasms, a clinically distinct syndrome from neonatal seizures, typically occur between 1 and 24 months after birth, and have a specific hypsarrhythmic EEG pattern and whole body "jack-knife" seizure pattern; hence, the target person for infantile spasms is typically more than 1, 2, 3 or 4 weeks old, and preferably under 36, 24 or 18 months. For refractory seizures the target person is typically at least 4, 6, 12, 16, 17 or 18 years old.

In another aspect the invention provides a method of treating a person in need thereof comprising coadministering to the person effective amounts of a γ-amino butyric acid (GABA) transaminase inhibitor and a Na—K—Cl cotransporter (NKCC1) inhibitor. In particular embodiments the person is determined to have had infantile spasms or refractory seizures as an adult. Coadministering means administering proximate in time, such that the NKCC1 inhibitor can reduce, prevent or attenuate one or more otherwise adverse side effects (such as retinal toxicity and intramyelinic edema) of the transaminase inhibitor. Generally, the NKCC1 inhibitor administration is coincident with, overlapping, or within 30, 10, 5, 3 or 1 day of transaminase inhibitor administration.

In another aspect the invention provides a method of treating a person treated or being treated with a γ-amino butyric acid (GABA) transaminase inhibitor, comprising administering to the person an effective amount of an NKCC1 inhibitor. In particular embodiments the person is determined to have had infantile spasms or refractory seizures as an adult. The NKCC1 is administered proximate in time to the transaminase pre-treatment such that the NKCC1 inhibitor can reduce, prevent or attenuate one or more otherwise adverse side effects (such as retinal toxicity and intramyelinic edema) of the transaminase inhibitor. Generally, the NKCC1 inhibitor administration is coincident with, overlapping, or within 360, 180, 90, 30, 10, 5, 3 or 1 day of transaminase inhibitor administration.

EXAMPLES

Example 1

Efficacy of bumetanide in a rat model of vigabatrin (VGB)-induced retinal toxicity.

For initial experiments we chose to evaluate outcome based on histopathology rather than electroretinograms, as we can better colocalize the cellular specificity of a protective effect. ERGs are variably correlated with histopathology in animal models, and for this reason we will concentrate on the pathologic lesion. Subsequent experiments evaluating ERG function confirm our results. We closely follow the methods of Duboc, et al (12) that recommend 30 days of treatment in juvenile rats to induce a lesion. Rats are treated with vehicle, VGB alone, or VGB+bumetanide, then eye cups prepared for histopathologic analysis, immunocytochemistry, and electron microscopy.

Model of VGB-induced toxicity. VGB is administered to young adult/juvenile Sprague Dawley rats between 6-7 weeks of age for a period of 30 days. VGB is dissolved in 0.9% NaCl at 100 mg/mL and injected intraperitoneally (i.p.) daily for 30 days at doses of 5 and 3 mg/day as described for treatment of animal epilepsy (26). These doses (250 or 150 mg/kg) are in the same range or lower than those prescribed to children (100 mg/kg, Bialer et al., 2001) or infants (250 mg/kg; 400 mg/kg) (27, 28).

Treatment groups. We use of 15 animals per group. Vehicle only, VGB alone, or VGB and bumetanide. The doses are daily. VGB is 5 mg/day and Bumetanide is applied i.p. at a dose of 0.1 mg/kg. The 0.1 mg/kg is dose is that which we found effective in the treatment of seizures in the immature brain, and is the same range per weight as that used in humans for diuresis. We also evaluate a higher dose of 0.2 mg/kg, which is at the high end of the range of doses used in humans for diuresis, to evaluate for optimal protective dose. Prior animal studies did not show significant diuresis in rats at these doses.

Histopathologic analysis of retina. As per established protocols eye cups are fixed overnight at 4° C. in 4% (wt/vol) paraformaldehyde in phosphate buffered saline PBS) 0.01M, pH 7.4. After cryoprotection in PBS containing successively 10, 20, and 30% sucrose at 4° C., the tissue is embedded in OCT (Labonord, Villeneuve d'Ascq, France). A preliminary analysis of general retinal morphology is performed on vertical sections (8-10 μm thickness) using hematoxylin and eosin. Additional sections are permeabilized for 5 minutes in PBS containing 0.1% Triton X-100 (Sigma, St. Louis, Mo.), rinsed, and incubated in PBS containing 1% bovine serum albumin (Eurobio, Les-Ulis, France), 0.1% Tween 20 (Sigma), and 0.1% sodium azide (Merck, Fontenay-Ss-Bois) for 2 hours at room temperature. The primary antibody is added to the solution and incubated for 2 hours at room temperature. Antibodies were anti-GFAP rabbit polyclonal antibody (1:400; DAKO), and antiactive caspase-3 rabbit polyclonal antibody (1:100; Cell Signaling Technology, Beverly, Mass.). After rinses, sections are incubated with the secondary antibody, goat anti-rabbit IgG conjugated to either Alexa™ 594 or Alexa™ 488 at 1 to 500 (Molecular Probes, Eugene, Oreg.) for 2 hours. Cone photoreceptors are stained with peanut agglutinin lectin coupled to Texas Red (PNA, 1:40; Sigma). DNA fragmentation is demonstrated with the In Situ End Labeling/terminal deoxy nucleotidyl transferase-mediated dUTP nick end labeling (ISEL/TUNEL) method (Roche Molecular Biochemicals, Penzburg, Germany). The dye, diamidiphenyl-indole (DAPI), is added to any incubation solution. Sections are mounted with Fluorsave reagent (Calbiochem, San Diego, Calif.). PNA-stained cone inner/outer segments are counted on retinal sections in eight consecutive 300 μm-wide optical windows on each side of the optic nerve under the 40× objective. Areas with a disorganized outer nuclear layer are specifically excluded from this count. Vertical sections are stained with hematoxylin and eosin.

NKCC1/KCC2 immunocytochemistry. As per our published methods (4), serial sections from retina are labeled with NKCC1 (1:100, Chemicon International) and KCC2 (1:200, Upstate) antibodies. To block nonspecific binding, sections were first incubated for 1 h at RT in a solution containing 0.1% Triton X-100 and 5% normal goat serum in PBS (Invitrogen). The sections were then exposed to primary antibodies overnight at 4° C. After 3×10 min wash in PBS, slides were incubated at RT with the secondary antibodies. For NeuN staining slides were incubated for 1 h with a secondary antibody solution containing Alexa Fluor 568 goat antimouse IgG (1:1000, Molecular Probes). For NKCC1 and KCC2 staining slides were incubated for 1 h with a biotinylated anti-rabbit IgG (1:200, Vector Laboratories), washed 3×10 min in PBS followed by 1 h incubation with an avidin-FITC conjugate (1:2000, Vector Laboratories). After secondary antibody incubation, sections were washed 3×10 min in PBS and cover-slipped with an anti-fade medium (Fluoromount-G, Southern Biotechnology).

To identify cell types expressing NKCC1 and KCC2, we use double labeling with a neuronal marker NeuN (1:100, Chemicon International), a glial marker (GFAP), and peanut agglutinin for cone photoreceptors. Control sections are incubated with omission of one or both primary antibodies, adding only both secondary antibodies to exclude false-positive labeling. Slides are analyzed using a fluorescence microscope (Zeiss Axioscope). The expression pattern of each antibody is analyzed on tissue sections processed in the same run.

Tissue Preparation for Electron Microscopy. Eye cups were fixed overnight at 4° C. in cacodylate 0.1M (Merck) containing 2% paraformaldehyde, 2.5% glutaraldehyde (Electron Microscopy Sciences, Hatfield, Pa.) and CaCl2 2.5 mM at pH 7.4. The tissue is rinsed in cacodylate 0.15M and postfixed in 1% osmium tetroxide (Electron Microscopy-Sciences) for 1 hour. After dehydration in ethanol, and propylene oxide, the tissue is embedded in epon. Semithin sections are stained with methylene blue and ultrathin sections (80 nm) contrasted with lead citrate and uranyl acetate.

Data analysis. For quantification we use the same outcome measures of retinal injury as Duboc et al and Jammoul et al (12, 25). Vertical sections along the dorsoventral axis are selected at the optic nerve. After DAPI nuclear staining, the lengths of disorganized retinal areas are measured; GFAP immunostaining is used for detection and quantification of retinal areas with reactive gliosis. The cone photoreceptor density is calculated after cone arrestin immunostaining to visualize the inner/outer segments of cone photoreceptors; areas with disorganized retinal layering were excluded. Treatment group means are compared using a one way ANOVA to determine whether bumetanide treatment improved outcome. To determine whether retinal injury colocalizes with NKCC1 expression, we evaluate NKCC1 expression in a semiquantitative scale with the different cell specific markers, as previously described in our published methods (29, 30) and those of Li et al (10).

Results. We are able to replicate the numerous studies that have used this model to demonstrate vigabatrin toxicity and we can visualize photoreceptor injury/loss and vacuolization. The lower dose of bumetanide (0.1 mg/kg) results in a significant decrease in toxicity, and our prior work has shown that this dose effectively suppresses NKCC1 in brain in rats. We see additional efficacy at the 0.2 mg/kg dose. We find no adverse effects of any modest diuresis at the higher dose, nor any significant effects on body weight or skin turgor.

Example 2

Validation of animal work demonstrating NKCC1 as a target for treatment of retinal injury: determining the distribution of NKCC1 and KCC2 in human retina from eye bank samples.

Acquisition of human retinal samples. We perform standard immunocytochemical analysis as outlined above for double labeling with neuronal and glial markers. Retinal sections are obtained from archives from children (n=8) and adults (n=5). In addition, we obtain freshly fixed (in 4% paraformaldehyde for 2 hours) eye tissue from discarded tissue in the Pathology and Ophthalmology departments at Children's Hospital and Massachusetts Eye and Ear Institute.

Immunocytochemical labeling for NKCC1 and KCC2. We perform this as described above, but evaluate in more detail the subcellular localization of NKCC1, similar to that of Li et al (10). In addition to double labeling for neurons, glia, and photoreceptor-specific markers, we also evaluate PSD-95 for the post synaptic terminals of photoreceptors and also SV2 for the presynaptic terminals. The presence of these further confirm that the NKCC1 transporter is functional in human retina.

Results. Human retina show patterns of NKCC1 expression similar to that described rodent in retina. This is novel data as no study has yet to report NKCC1 or KCC2 expression in human retinal cells. We see expression in retinal cell types including the photoreceptors and bipolar cells.

Example 3

Bumetanide decreases white matter injury and vacuolation in the rodent model of VGB-induced IME.

Model of VGB-induced IME. We adhere to the same protocol used by Ovation in recent studies. Sprague Dawley rat pups are treated from postnatal day 4-25 with VBG (50 mg/kg) or vehicle. This is administered by oral gavage to rats starting on PND 4. The single dose of 50 mg/kg was selected on the basis of the previous study in which it produced vacuolar lesions (24, 31). Rats are sacrificed at P25 and perfused with 4% paraformaldehyde. Brains are cryoprotected in sucrose for frozen sectioning.

Treatment groups. We use an n of 15 animals per group. Vehicle only, VGB alone, or VGB and bumetanide. The doses are daily. VGB is 50 mg/kg/day and Bumetanide is applied i.p. at a dose of 0.1 mg/kg/day. The 0.1 mg/kg dose is that which we have found effective in the treatment of seizures in the immature brain, and is the same range per weight as that used in humans for diuresis. We also evaluate a higher dose of 0.2 mg/kg, which is at the high end of the range of doses used in humans for diuresis, to evaluate for optimal protective dose. Prior animal studies did not show significant diuresis in rats at these doses.

Histological and immunocytochemical methods. Using our published protocols for quantification of white matter myelination (29) we perform MBP staining. 16 µm coronal cryostat sections (Leica CM3050 S) were collected on Superfrost Plus slides. For NMDAR expression in normal rat brain and human parietal lobe, 50 µm freezing microtome (HM 440E, Microm International) free-floating sections were collected. Hematoxylin and eosin (H&E) staining was performed according to standard protocols. Immunocytochemical studies are performed as previously described (32, 33). The following primary antibodies were used: mouse monoclonal antibodies to MBP/SMI-99, and glial fibrillary acidic protein (GFAP)/SMI-22 (Sternberger Monoclonals/Covance Lutherville, Md.), mouse monoclonal IgM antibodies to O4 and O1 (gifts of Dr. S. Pfeiffer, Farmington, Conn.), mouse monoclonal antibody to CD68/MCA341GA and CD11b/MCA275G (Serotec Raleigh, N.C.), mouse monoclonal antibody to NeuN/MAB 377, and rabbit polyclonal antibody to NR1/AB1516 (Chemicon International/Millipore). Sections are blocked and incubated overnight at 4° C. with the primary antibody. Fluorescent goat Alexa Fluor 488 or 568 secondary antibodies (Molecular Probes/Invitrogen Carlsbad, Calif.) appropriate to the primary antibody species are applied for 1 hr at room temperature. For NR1, a biotinylated anti-rabbit IgG followed by an avidin-FITC conjugate (Vector Laboratories, Burlingame, Calif.) was applied.

To assess whether there are alterations in proliferating and immature oligodendrocytes, we use the O4 marker. Double labeling was performed sequentially with O4 (detergent free). Slides were coverslipped with an antifade medium (Fluoromount-G; Southern Biotechnology, Birmingham, Ala.) or a mounting medium containing nuclear stain DAPI (Vector Laboratories).

Tissue Preparation for Electron Microscopy. A subset of animals (n=8 per group) is perfused with glutaraldehyde for qualitative evaluation of intramyelinic edema. White matter samples from corpus callosum and cerebellum are fixed overnight at 4° C. in cacodylate 0.1M (Merck) containing 2% paraformaldehyde, 2.5% glutaraldehyde (Electron Microscopy Sciences, Hatfield, Pa.) and CaCl2 2.5 mM at pH 7.4. The tissue is rinsed in cacodylate 0.15M and postfixed in 1% osmium tetroxide (Electron Microscopy Sciences) for 1 hour. After dehydration in ethanol, and propylene oxide, the tissue is embedded in epon. Semi-thin sections are stained with methylene blue and ultrathin sections (80 nm) contrasted with lead citrate and uranyl acetate.

NKCC1 and KCC2 expression in brain white matter. We also study the cellular localization of NKCC1 and KCC2 in normal white matter from age-matched control rats. We use our published protocols for immunocytochemistry as described above, and include double labeling for mature (MBP) and immature oligodendrocytes (O4) markers (29).

Data analysis. Fluorescence images are obtained on a Zeiss Axioscope, using a Spot digital camera and Advanced 4.5 software (Diagnostic Instruments). Coronal sections in the region of the mid-dorsal hippocampus are examined for alterations in cortical, hippocampal, corpus callosal and thalamic white matter. A posterior section in the region of the cerebellum is used for analysis of brainstem and cerebellar myelination. ImageJ software is used to quantitate MBP and O4 immunostaining as a proportion of the white matter capsule area (29). This methodology was validated with ImageJ software quantitation of total area of MBP immunostaining within each 2.4 mm2 field. ImageJ analysis of immunocytochemical staining is represented as a ratio of ipsilateral (to ischemia) to contralateral staining to take account of inter-animal developmental variations. MBP staining was scored using a 5 point semi-quantitative ranked injury score modified from our previous 3 point scale (34): 0=no MBP loss; 1=some loss of processes perpendicular to capsule; 2=moderate loss of processes; 3=complete loss of processes with intact capsule; 4=loss of processes with thinning or breaks in capsule; 5=loss of processes with complete loss of capsule. Treatment groups are compared by a one way ANOVA.

Results. Similar to Example 1 the lower dose of bumetanide shows protective efficacy consistent with our prior experience with CNS efficacy at these doses. In addition we see additional efficacy at the higher dose. Also, these doses have previously shown no significant dehydration.

Example 4

Exemplary Coformulated Effective Combination Therapies

| | |
|---|---|
| A1. ethanolamine-O-sulfate, bumetanide | A2. ethanolamine-O-sulfate, furosemide |
| B1. γ-acetylenic-GABA, bumetanide | B2. γ-acetylenic-GABA, furosemide |
| C1. aminooxyacetic acid, bumetanide | C2. aminooxyacetic acid, furosemide |
| D1. vigabatrin, bumetanide | D2. vigabatrin, furosemide |
| D3. vigabatrin, ethacrynic acid | D4. vigabatrin, torsemide |
| E1. valproate, bumetanide | E2. valproate, furosemide |
| F1. 4-hydroxybenzaldehyde, bumetanide | F2. 4-hydroxybenzaldehyde, furosemide |
| G1. 3-chloro-1-(4-hydroxyphenyl)propan-1-one, bumetanide | G2. 3-chloro-1-(4-hydroxyphenyl)propan-1-one, furosemide |
| H1. 4-acryloylphenol, bumetanide | H2. 4-acryloylphenol, furosemide |

REFERENCES

1. Engel J, Pedley T A. Epilepsy: a comprehensive textbook, 2nd ed. Philadelphia: Wolters Kluwer Health/Lippincott Williams & Wilkins, 2008.
2. Volpe J J. Neurology of the newborn, 5th ed. Philadelphia: Saunders/Elsevier, 2008.
3. Silverstein F S, Jensen F E. Neonatal seizures. Ann. Neurol. 2007; 62:112-120.
4. Dzhala V I, Talos D M, Sdrulla D A, Jensen, F E, Staley. Nat. Med. 2005; 11:1205-1213.
5. Dzhala V I, Brumback A C, Staley K J. Ann. Neurol. 2008; 63:222-235.
6. Neal M J, Cunningham J R, Shah M A, Yazulla S. Neurosci Lett 1989; 98:29-32.
7. Cubells J F, Blanchard J S, Smith D M, Makman M H. J Pharmacol Exp Ther 1986; 238:508-514.
8. Kahle K T, Staley K J. Neurosurg Focus 2008; 25:E22.
9. Lopez-Samblas A M, Adams J A, Goldberg R N, Modi M W. Biol Neonate 1997; 72:265-272.
10. Li B, McKernan K, Shen W. V is Neurosci 2008; 25:109-123.
11. Thoreson W B, Bryson E J, Rabl K. J Neurophysiol 2003; 90:1747-1753.
12. Duboc A, Hanoteau N, Simonutti M, et al. Ann. Neurol. 2004; 55:695-705.
13. Crewther S G, Murphy M J, Crewther D P. PLoS ONE 2008; 3:e2839.
14. Putney L K, Brandt J D, O'Donnell M E. Invest Ophthalmol V is Sci 1999; 40:425-434.
15. Noell W K, Walker V S, Kang B S, Berman S. Invest Ophthalmol 1966; 5:450-473.
16. Stotzer H, Weisse I, Knappen F, Seitz R. Arzneimittelforschung 1970; 20:811-817.
17. Bauer B. Acta Ophthalmol (Copenh) 1978; 56:270-281.
18. Versaux-Botteri C, Wasowicz M, Morice-Davoine C, Ferrari P. Aventis Report, 2001-0467.
19. Versaux-Botteri C, Wasowicz M, Morice-Davoine C, Ferrari P. Aventis Report, 2001-0465.
20. Chalier C, Guffroy M, Guilpin V, Joly A. Aventis Report, Unpub 2001-1068.
21. Foss J. Ovation Pharm Study No. OV-1007, CRL Study No. DMQ00001.
22. Wang Q P, Jammoul F, Duboc A, et al. Eur J Neurosci 2008; 27:2177-2187.
23. Ochoa-de la Paz L D, Lezama R, Toscano B, Pasantes-Morales H. Pflugers Arch 2005; 449:526-536.
24. Jom R, Rimmer E M, Williams J (1987) Micro-Vacuolation In Rat Brains After Long Term Administration Of Gaba-Transaminase Inhibitors.
25. Jammoul F, Wang Q, Nabbout R, Coriat C, Duboc A, Simonutti M, Dubus E, Craft C M, Ye W, Collins S D, Dulac O, Chiron C, Sahel J A, Picaud S (2009) Taurine deficiency is a cause of vigabatrin-induced retinal phototoxicity. Ann Neurol 65:98-107.
26. Andre V, Ferrandon A, Marescaux C, Nehlig A (2001) Vigabatrin protects against hippocampal damage but is not antiepileptogenic in the lithium-pilocarpine model of temporal lobe epilepsy. Epilepsy Res 47:99-117.
27. Aicardi J, Mumford J P, Dumas C, Wood S (1996) Vigabatrin as initial therapy for infantile spasms: a European retrospective survey. Sabril IS Investigator and Peer Review Groups. Epilepsia 37:638-642.
28. Bialer M, Johannessen S I, Kupferberg H J, Levy R H, Perucca E, Tomson T (2004) Progress report on new antiepileptic drugs: a summary of the Seventh Eilat Conference (EILAT VII). Epilepsy Res 61:1-48.
29. Follett P L, Deng W, Dai W, Talos D M, Massillon L J, Rosenberg P A, Volpe J J, Jensen F E (2004) Glutamate receptor-mediated oligodendrocyte toxicity in periventricular leukomalacia: A protective role for topiramate. J Neurosci 24 4412-4420.
30. Manning S M, Talos D M, Zhou C, Selip D B, Park H K, Park C J, Volpe J J, Jensen F E (2008) NMDA receptor blockade with memantine attenuates white matter injury in a rat model of periventricular leukomalacia. J Neurosci 28:6670-6678.
31. Sills G J (2003) Pre-clinical studies with the GABAergic compounds vigabatrin and tiagabine. Epileptic Disord 5:51-56.
32. Talos D M, Fishman R E, Park H, Folkerth R D, Follett P L, Volpe J J, Jensen F E (2006a) Developmental regulation of alpha-amino-3-hydroxy-5-methyl-4-isoxazole-propionic acid receptor subunit expression in forebrain and relationship to regional susceptibility to hypoxic/ischemic injury. I. Rodent cerebral white matter and cortex. J Comp Neurol 497:42-60.
33. Talos D M, Follett P L, Folkerth R D, Fishman R E, Trachtenberg F L, Volpe J J, Jensen F E (2006b) Developmental regulation of alpha-amino-3-hydroxy-5-methyl-4-isoxazole-propionic acid receptor subunit expression in forebrain and relationship to regional susceptibility to hypoxic/ischemic injury. II. Human cerebral white matter and cortex. J Comp Neurol 497:61-77.
34. Follett P L, Rosenberg P A, Volpe J J, Jensen F E (2000) NBQX attenuates excitotoxic injury in developing white matter. J Neurosci 20:9235-9241.

The invention encompasses all recombinations of alternative elements or components as if each recombination were individually and belaboredly set forth herein. The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of attenuating a retinal toxicity or an intramyelinic edema side effect of vigabatrin therapy comprising co-administering to a person in need thereof an effective amount of vigabatrin and bumetanide.

2. The method of claim 1 wherein the person is determined to have had infantile spasms or refractory seizures as an adult.

3. The method of claim 1, wherein vigabatrin and bumetanide are administered to the person in a single dosage form.

4. The method of claim 1, wherein the person is administered a dosage form of vigabatrin and a dosage form of bumetanide.

5. The method of claim 1, wherein the person is administered a dose of 50mg/kg to 150 mg/kg vigabatrin.

6. The method of claim 1, wherein the person is administered a dose of 0.1mg/kg to 0.2 mg/kg bumetanide.

7. The method of claim 1, wherein the person is administered a dose of 50mg/kg to 150 mg/kg vigabatrin and a dose of 0.1 mg/kg to 0.2 mg/kg vigabatrin.

8. The method of claim 4, wherein the dosage form of vigabatrin contains 100mg to 1000 mg of vigabatrin and the dosage form of bumetanide contains 0.2 mg to 3.0 mg bumetanide.

9. The method of claim 8, wherein the dosage form of vigabatrin contains 200mg to 800 mg vigabatrin and the dosage form of bumetanide contains 0.2 mg to 0.5 mg bumetanide.

10. The method of claim 8, wherein the dosage form of vigabatrin contains 500mg vigabatrin.

11. The method of claim 9, wherein the dosage form of vigabatrin contains 500mg vigabatrin.

* * * * *

UNITED STATES PATENT AND TRADEMARK OFFICE
CERTIFICATE OF CORRECTION

PATENT NO. : 8,822,539 B2  
APPLICATION NO. : 13/069311  
DATED : September 2, 2014  
INVENTOR(S) : Frances E Jensen Page 1 of 1

It is certified that error appears in the above-identified patent and that said Letters Patent is hereby corrected as shown below:

On the title page, column 2 References cited (Other Publications), line 6, delete "Left.," and insert -- Lett., --

On the title page, column 2 References cited (Other Publications), line 49, delete "Left.," and insert -- Lett., --

In the Claims

In column 13, line 18, claim 5, delete "50mg/kg" and insert -- 50 mg/kg --

In column 14, line 2, claim 6, delete "0.1mg/kg" and insert -- 0.1 mg/kg --

In column 14, line 4, claim 7, delete "50mg/kg" and insert -- 50 mg/kg --

In column 14, line 7, claim 8, delete "100mg" and insert -- 100 mg --

In column 14, line 11, claim 9, delete "200mg" and insert -- 200 mg --

In column 14, line 15, claim 10, delete "500mg" and insert -- 500 mg --

In column 14, line 17, claim 11, delete "500mg" and insert -- 500 mg --

Signed and Sealed this
Twenty-first Day of April, 2015

Michelle K. Lee
*Director of the United States Patent and Trademark Office*